United States Patent [19]

Williamson et al.

[11] 4,243,825

[45] Jan. 6, 1981

[54] DEHYDROCOUPLING OF TOLUENE

[75] Inventors: Alex N. Williamson, Greensboro, N.C.; Samuel J. Tremont, Manchester, Mo.

[73] Assignee: Monsanto Company, St. Louis, Mo.

[21] Appl. No.: 101,930

[22] Filed: Dec. 10, 1979

[51] Int. Cl.³ .............................................. C07C 2/72
[52] U.S. Cl. .................................. 585/428; 252/463; 585/422
[58] Field of Search ....................... 585/428, 426, 422; 252/463

[56] References Cited

U.S. PATENT DOCUMENTS

| | | | |
|---|---|---|---|
| 3,476,747 | 11/1969 | Hargis et al. | 585/426 |
| 3,494,956 | 2/1970 | Greene et al. | 585/428 |
| 3,557,235 | 1/1971 | Henry et al. | 585/428 |
| 3,694,518 | 9/1972 | Franz et al. | 585/428 |
| 3,868,427 | 2/1975 | Franz | 585/428 |
| 3,963,793 | 6/1976 | Weterings | 585/428 |
| 3,965,206 | 6/1976 | Montgomery et al. | 585/428 |
| 3,980,580 | 9/1976 | Fox et al. | 252/463 |
| 4,091,044 | 5/1978 | Li | 585/428 |
| 4,117,021 | 9/1978 | Hupp et al. | 585/428 |

FOREIGN PATENT DOCUMENTS 1538670  1/1979  United Kingdom .

OTHER PUBLICATIONS

S. S. Hupp et al., Ind. Eng. Chem. Prod. Res. Div., vol. 18, No. 2, pp. 117-122, 1979.
F. C. Lorenz, Chem. Ber., vol. 7, pp. 1096-1098, 1874.
Arno Behr et al., Chem. Ber., vol. 6, pp. 753-755, 1873.

*Primary Examiner*—Veronica O'Keefe
*Attorney, Agent, or Firm*—Wendell W. Brooks; James C. Logomasini; Stanley M. Tarter

[57] ABSTRACT

Toluene dehydrocoupled products are produced by heating toluene in the vapor phase with an inorganic metal/oxygen composition which functions as an oxygen carrier and has the empirical formula:

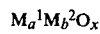

$$M_a^1 M_b^2 O_x$$

where $M^1$ is thallium and $M^2$ is at least one element selected from arsenic, antimony, thorium, uranium, the lanthanides or rare earths, Groups 3b, 4b, 5b, and 7b of the Periodic Table of the Elements, and mixtures thereof, and wherein a is 1, b is 0.01 to 10, and x is a number taken to satisfy the average valences of $M^1$ and $M^2$ in the oxidation states in which they exist in the composition. Alternatively, the same inorganic metal-/oxygen composition can be employed as a catalyst or as a combination catalyst/oxygen carrier for the dehydrocoupling reaction when oxygen or an oxygen-containing gas is heated with the toluene.

17 Claims, No Drawings

DEHYDROCOUPLING OF TOLUENE

FIELD OF THE INVENTION

This invention relates to the production of dehydrocoupled toluene products. It is particularly related to the oxidative synthesis of 1,2-diphenylethylene (stilbene) from toluene and to inorganic metal/oxygen compositions effective for oxidatively coupling toluene to produce stilbene.

Stilbene, because of its unsaturated character is very reactive and may be employed in various organic syntheses. Derivatives of stilbene are useful in the production of products which may be used in the manufacture of dyes, paints and resins. It is also useful in optical brighteners, in pharmaceuticals, and as an organic intermediate.

DESCRIPTION OF THE PRIOR ART

Dehydrocoupling of toluene by the reaction with lead oxide to form stilbene has been reported by Behr and Van Dorp, *Chem. Ber.*, 6, 753 (1873) and Lorenz, *Chem. Ber.*, 7, 1996 (1874). In this reported work, stilbene is obtained by conveying toluene over lead oxide maintained at or about at a dark red glow. The coupling of toluene using elemental sulfur as the coupling agent has been reported by Renard, *Bull. Soc. Chim. France*, 3, 958 (1889); 5, 278 (1891) and the types of products produced by such coupling reactions have been discussed by Horton, *J. Org. Chem.*, 14, 761 (1949). More recently, U.S. Pat. No. 3,476,747 discloses arsenic pentoxide, antimony tetroxide, antimony pentoxide, bismuth trioxide, and manganese arsenate as oxidants for the oxidative dehydrocoupling of toluene to form 1,2-bis-(aryl)ethylenes. Similarly, U.S. Pat. No. 3,494,956 discloses lead oxide, cadmium oxide, and thallium oxide as suitable oxidants, and in Example 9 a mixture of toluene and oxygen passed over heated lead oxide produced bibenzyl. In U.S. Pat. No. 3,557,235 the stoichiometric toluene coupling reaction is taught using an oxide of bismuth, lead, tellurium, barium, thallium, cadmium, or mixtures thereof which serves as the source of oxygen in the reaction. U.S. Pat. No. 3,963,793 teaches the use of bismuth trioxide and thallium trioxide or mixtures thereof supported on basic carrier materials selected from the oxides of Group 2a elements and having a minimun surface area of 20 m$^2$/g as suitable for toluene coupling to produce bibenzyl. The addition to the supported catalyst of small amounts of silver as a promoter is also disclosed. In U.S. Pat. No. 3,965,206 oxides of lead, cadmium, bismuth, and mixtures thereof are taught as suitable oxidants for toluene coupling. This patent also teaches the disproportionation of the stilbene with ethylene to produce styrene. U.S. Pat. No. 3,980,580 discloses an oxygen composition of lead, magnesium, and aluminum as an oxidant for toluene coupling. Also, U.S. Pat. No. 4,091,044 discloses oxygen compositions of lead and antimony and optionally with bismuth as oxidants for toluene coupling to form stilbene.

SUMMARY OF THE INVENTION

This invention is directed to a process for the oxidative dehydrocoupling of toluene and toluene derivatives to stilbene and stilbene derivatives. In another aspect, this invention is directed to inorganic metal/oxygen compositions which are useful as the oxygen source for the oxidative dehydrocoupling of toluene to produce stilbene, or alternatively as catalysts or combination catalysts/oxygen source for the dehydrocoupling reaction when oxygen or an oxygen-containing gas is heated with the toluene.

Accordingly, typical objects of this invention are to provide (1) inorganic metal/oxygen compositions useful as the oxygen source in oxidative dehydrocoupling of toluene and toluene derivatives, (2) inorganic metal/oxygen compositions useful as catalysts in the oxidative dehydrocoupling of toluene and toluene derivatives, (3) inorganic metal/oxygen compositions useful as combination catalysts/oxygen source in the oxidative dehydrocoupling of toluene and toluene derivatives, (4) a one-step, vapor phase process for the production of stilbene and stilbene derivatives and bibenzyl and bibenzyl derivatives, and (5) a one-step, vapor phase dehydrocoupling process for converting toluene and toluene derivatives to stilbene and stilbene derivatives characterized by high toluene conversions and high stilbene slectivities.

These and other objects and advantages of this invention are achieved by the process disclosed herein for dehydrocoupling toluene and toluene derivatives. Toluene dehydrocoupled products are produced by heating toluene (and toluene derivatives) in the presence of an inorganic metal/oxygen composition which functions in a catalytic mode, a stoichiometric mode as an oxidant or oxygen carrier, or a combined catalytic/stoichiometric mode for the dehydrocoupling reaction.

DESCRIPTION OF THE PREFERRED EMBODIMENTS

In accordance with this invention, toluene and toluene derivatives are dehydrocoupled by a process which comprises contacting the toluene (and toluene derivatives) in the vapor phase at a temperature between about 450° C. and about 650° C. with an inorganic metal/oxygen composition represented by the empirical formula:

$$M_a^1 M_b^2 O_x$$

where $M^1$ is thallium and $M^2$ is at least one element selected from arsenic, antimony, thorium, uranium, the lanthanides or rare earths, Groups 3b, 4b, 5b, and 7b of the Periodic Table of the Elements, and mixtures thereof, and wherein a is 1, b is 0.01 to 10, and x is a number taken to satisfy the average valences of $M^1$ and $M^2$ in the oxidation states in which they exist in the composition to yield the dehydrocoupled toluene product. The inorganic metal/oxygen composition functions in a catalytic mode, a stoichiometric mode as an oxidant or oxygen carrier, or a combined catalytic/stoichiometric mode for the dehydrocoupling of toluene.

In the catalytic mode of operation, oxygen or an oxygen-containing gas such as air or oxygen-enriched air is reacted with toluene in the presence of the inorganic metal/oxygen composition in an amount sufficient for the dehydrocoupling reaction. In the stoichiometric mode of operation, the inorganic metal/oxygen composition is the sole source of oxygen. That is, in the latter instance the dehydrocoupling of toluene is conducted in the substantial absence of added free oxygen such as would be obtained from air. In the combined catalytic/stoichiometric mode of operation, oxygen or an oxygen-containing gas is added as a reactant in a manner similar to that noted hereinabove for the catalytic mode of operation. However, the amount of added oxygen is not sufficient for the dehydrocoupling reaction and the required additional oxygen must be supplied by the inorganic metal/oxygen composition.

Of these three modes of operation, the stoichiometric mode is generally preferred in that undesirable side reactions—oxidative dealkylation, for example, to produce benzene and carbon dioxide—are substantially reduced. It will, of course, be recognized that in spite of the undesirability of producing benzene during the course of the reaction of the present process, benzene is a valuable article of commerce. It is therefore highly desirable to recover the benzene values when substantial production thereof occurs. The recovery and purification of such benzene values may be accomplished by any standard method and means known to the art.

The term "dehydrocoupling" and related terms are employed herein to mean that the toluene molecules are coupled or dimerized—with carbon-carbon bond formation occurring between the methyl group carbons—and the coupled molecules have lost either one or two hydrogen atoms from the methyl group of each toluene molecule. When two hydrogen atoms per molecule of toluene are lost, the carbon-carbon bond at the coupling or dimerization site is unsaturated as by dehydrogenation, that is, stilbene is the product. On the other hand, bibenzyl, having a saturated carbon-carbon bond at the coupling site, is the product when only one hydrogen atom per molecule of toluene is lost.

In general, the production of stilbene as the dehydrocoupled toluene product is preferred over the production of bibenzyl. This stated preference is due to the unsaturated character of bibenzyl. And, as is well known to the art, the presence of the unsaturated olefinic carbon-carbon double bond causes the stilbene to exhibit high reactivity, thereby facilitating its direct use as an organic intermediate in numerous organic syntheses.

The process of this invention is conveniently carried out in an apparatus of the type suitable for carrying out chemical reactions in the vapor phase. It can be conducted in a single reactor or in multiple reactors using either a fixed bed, a moving bed, or a fluidized bed system to effect contacting of the reactant or reactants and inorganic metal/oxygen composition. The reactant toluene or toluene derivative will generally be heated and introduced into the reactor as a vapor. However, the reactant may be introduced to the reactor as a liquid and then vaporized.

The oxidative dehydrocoupling reaction is carried out in the vapor phase and under the influence of heat. The temperature range under which the reaction can be carried out ranges from about 450° C. to about 650° C. and preferably is conducted at from about 500° C. to about 600° C.

Pressure is not critical in the process of this invention. The reaction may be carried out at subatmospheric, atmospheric, or superatmospheric pressures as desired. It will be generally preferred, however, to conduct the reaction at or near atmospheric pressure. Generally, pressures from about $2.53 \times 10^4$ pascals or Pa (0.25 atmosphere or atm) to about $4.05 \times 10^5$ Pa (4.0 atm) may be conveniently employed.

The reaction time for the contact of the reactant with the inorganic metal/oxygen composition in this invention may be selected from a broad operable range which may vary from about 0.1 to about 60 seconds. The reaction time may be defined as the length of time in seconds which the reactant gases measured under reaction conditions are in contact with the inorganic metal/oxygen composition in the reactor. The reaction time may vary depending upon the reaction temperature and the desired toluene conversion level. At higher temperatures and lower toluene conversion levels, shorter contact times are required. Generally, the contact time will vary from about 0.5 second to about 20 seconds. Preferably, for optimum conversion and selectivity in the preferred temperature range, a contact time from about 1 second to about 12 seconds is employed.

In addition to the toluene and/or toluene derivatives, other inert substances such as nitrogen, helium, and the like may be present in the reactor. Such inert materials may be introduced to the process alone or may be combined with the other materials as feed. Water or steam may be added to the reaction zone, preferably being introduced with the feed in order to improve the selectivity to the desired products and particularly to suppress complete oxidation to $CO_2$. Steam-to-hydrocarbon ratios in the range from 0.1 to 10 or more are suitable, the upper limit being determined by practical cost considerations. Ratios in the range from 0.5 to 3 are preferred.

The inorganic metal/oxygen composition suitable for use in this invention contains oxygen in such a manner that it is capable of releasing stoichiometric quantities of oxygen under the oxidative reaction conditions employed. The oxygen in the composition is associated with the metals as oxides, as oxygen complexes of at least two of the metals present, or as mixtures of oxides and complexes. The inorganic metal/oxygen composition can be represented by the empirical formula:

$$M_a^1 M_b^2 O_x$$

where $M^1$ is thallium (from Group 3a); $M^2$ is at least one element selected from the group of scandium, yttrium, lanthanum, and actinium of Group 3b; titanium, zirconium, and hafnium of Group 4b; vanadium, niobium, and tantalum of Group 5b; manganese, technetium, and rhenium of Group 7b; arsenic and antimony of Group 5a; cerium, praseodymium, neodymium, promethium, samarium, europium, gadolinium, terbium, dysprosium, erbium, thulium, ytterbium, and lutetium, of the lanthanides or rare earths; and thorium and uranium of the actinides, and mixtures thereof, and wherein a is 1, b is 0.01 to 10, and x is a number taken to satisfy the average valences of $M^1$ and $M^2$ in the oxidation states in which they exist in the inorganic metal/oxygen composition. Preferred compositions are those represented by the above-noted empirical formula wherein a is 1, b is 0.5 to 5 and x is a number taken to satisfy the average valences of $M^1$ and $M^2$ in the oxidation states in which they exist in the composition.

Of the $M^2$ elements listed, tantalum, antimony, and those from Group 4b of the Periodic Table of the Elements, and mixtures thereof, are preferred, with titanium of Group 4b being most preferred.

The term "Periodic Table of the Elements" as employed herein refers to the Periodic Table of the Elements published in CRC Handbook of Chemistry and Physics, 59th ed., Weast, Ed., CRC Press, Inc., West Palm Beach, FL 1978, Inside Front Cover.

The inorganic metal/oxygen composition may be employed in this invention alone or in association with a support or carrier. The use of a support may be particularly advantageous where the composition is too soft or attrition-prone to retain its structural integrity during reactor charging and/or under reaction conditions encountered during the course of the reaction process. Suitable supports for the compositions are, for example, silica, alumina, silica-alumina, metal aluminates such as magnesium aluminate, calcium aluminate, and the like.

As noted hereinabove, the dehydrocoupling reaction may be conducted in the presence or absence of added free oxygen. When oxygen is not added to the system, that is, the reaction is conducted in the stoichiometric mode of operation, the oxygen required for the reaction is provided by the inorganic metal/oxygen composition which enters into the reaction and is consequently reduced (or, in actual practice, partially reduced) during the course of the reaction. This necessitates regeneration or re-oxidation which can be easily effected by heating the material in air or oxygen at temperatures from about 500° C. to about 650° C. for a period of time ranging from about 5 seconds to about one hour. In a semi-continuous operation, regeneration can be effected by periodic interruption of the reaction for re-oxidation of the reduced composition, that is, periods of reaction are cycled with periods of regeneration. Operation, however, can be on a continuous basis whereby a portion of the inorganic metal/oxygen composition can be continuously or intermittently removed, re-oxidized and the re-oxidized material can thereafter be continuously or intermittently returned to the reaction. The latter method is particularly adapted to operations in which the inorganic metal/oxygen composition is fed in the form of a fluidized bed or a moving bed system.

When oxygen is employed as a reactant, the reaction may be conducted in either a catalytic mode or operation, depending on the amount of oxygen supplied. In the catalytic mode of operation, oxygen is supplied in an amount sufficient for the dehydrocoupling reaction. The actual amount of oxygen supplied may be specified as a function of the amount of the toluene or other suitable hydrocarbon component. On this basis the amount of oxygen supplied is ordinarily selected to provide a hydrocarbon-to-oxygen mole ratio from about 1 to about 8 and preferably from about 2 to about 6.

In the combined catalytic/stoichiometric mode of operation, the amount of oxygen supplied as a reactant is not sufficient for the dehydrocoupling reaction, thereby requiring an additional source of oxygen. The required additional oxygen will be supplied by the inorganic metal/oxygen composition, that is, the composition will serve as the additional source of oxygen. As a result, the inorganic metal/oxygen composition enters into the reaction and is consequently reduced during the course of the reaction. This necessitates regeneration or re-oxidation of the reduced composition which can be easily effected as described hereinabove for the stoichiometric mode of operation.

In either mode of operation employing added oxygen as a reactant, whether catalytic or combined catalytic/stoichiometric, the added free oxygen may be supplied either as oxygen or an oxygen-containing gas such as air or oxygen-enriched air.

The inorganic metal/oxygen compositions can be prepared in several ways. The simplest method involves intimately mixing the powdered metal oxides in the dry state and calcining. Another method involves adding the metal oxides to water with stirring, filtering to remove excess water or, alternatively, heating to evaporate the water, drying, and calcining. In another method of preparation, the powdered metal oxides can be intimately mixed before forming a paste of them with water and further mixing the paste. The paste can be spread and dried in air, after which it can be calcined in air. The calcined product can then be crushed and sieved to the desired mesh size. In still another method of preparation, the powdered metal oxides can be mixed in the dry state together with a material which facilitates forming the mixture into pellets and then pressed to form pellets which are calcined prior to use. A further method of preparation involves intimately mixing the powdered metal oxides in water and spray drying the resulting slurry or solution to produce relatively dust-free and free-flowing spherical particles which are also calcined prior to use.

In an alternative method of preparation, suitable inorganic metal/oxygen composition precursor salts such as nitrates, carbonates, and acetates are intimately mixed or dissolved in water or nitric acid and heated to thermally decompose the precursor salts to form the corresponding oxides and/or oxygen complexes. The oxides and/or oxygen complexes can then be treated as described hereinabove prior to use.

Temperatures employed for calcination of the inorganic metal/oxygen composition may vary from about 400° C. to about 1200° C. The higher temperatures from about 900° C. to about 1100° C. result in higher selectivity with some loss in activity. Preferred calcination temperatures, therefore, lie in the range from about 700° C. to about 1000° C. Calcination times may vary from about 1 hour to about 12 hours or more and preferably from about 2 hours to about 10 hours at the higher temperatures. The surface area of the composition is not critical. In general, however, a surface area less than about 10 $m^2/g$ is preferred, with values between about 0.1 $m^2/g$ and about 5 $m^2/g$ being most preferred.

As previously indicated, the process of this invention is preferably carried out in the absence of added free oxygen, that is, in the stoichiometric mode of operation, and utilizes only that oxygen supplied by the inorganic metal/oxygen composition. Also, with few exceptions, at substantially comparable conditions, the lower the toluene conversion level, the higher will be the selectivity to the dehydrocoupled products. That is, under similar conditions, the selectivity to the dehydrocoupled toluene products is in general inversely proportional to the toluene conversion level. However, for practical reasons, the dehydrocoupling reaction will generally be conducted at a toluene conversion level of about 20 to about 55 percent.

The dehydrocoupled toluene products, stilbene and bibenzyl, may be recovered and purified by any appropriate method and means known to the art and further elucidation here will be unnecessary duplication of the art. As noted previously, stilbene, of course, is the preferred product.

The following specific examples illustrating the best presently-known methods of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1

Procedure A

A series of inorganic metal/oxygen compositions having varied $Tl/M^2$ atomic ratios were prepared by intimately mixing the appropriate amount in grams of thallium (III) oxide ($Tl_2O_3$) and at least one $M^2$ oxide (or hydroxide) or nitrate in water and then heating to evaporate the water and decompose the nitrates when employed. The resulting solid was placed in an open casserole dish and calcined in air for an initial period at an initial temperature and then at a final temperature for an additional period. The calcined material was removed from the oven, cooled, crushed in a mortar, and sieved to 14/30 mesh particles for evaluation in the toluene conversion reactor described in Example 3 below. The parameters for such compositions, conveniently designated as 1-A-, are set forth in Table 1.

Procedure B

The procedure described in Procedure A above was employed except that following the final calcination, the calcined material was removed from the oven, cooled, crushed, and mixed with a calcium aluminate cement (Alcoa-CA-25) in an amount corresponding to 25% by weight of the dry weight of the calcined material. The resulting solid mixture was slurried with water to form a thick paste and allowed to air dry. The air-dried paste was calcined in air in an open casserole dish for 2 hours at 400° C. and then at a final temperature of 700° C. for an additional 2 hours. The supported inorganic metal/oxygen composition was removed from the oven, cooled, crushed in a mortar, and sieved to 14/30 mesh particles for evaluation in the toluene conversion reactor described in Example 3 below. The parameters for such compositions, conveniently designated as 1-B-, are set forth in Table 1.

EXAMPLE 2

A series of inorganic metal/oxygen compositions containing two or more $M^2$ elements can be prepared by the following described procedure. Dissolve or intimately mix the appropriate amount in grams of thallium (III) oxide ($Tl_2O_3$) or thallium (III) nitrate [$Tl(NO_3)_3$] and at least two $M^2$ oxides or nitrates (or alternatively, mix an appropriate amount of a suitable thallium-containing binary inorganic metal/oxygen composition with at least one $M^2$ oxide or nitrate) in water and heat to evaporate the water and decompose the nitrates, when employed. Place the resulting solid in an open casserole dish and calcine in air for an initial period at an initial temperature and then at a final temperature for an additional period (usually 1 hour at 400° C. and 700° C. for 12 hours, respectively). Remove the calcined material from the oven, cool, crush in a mortar, and sieve to 14/30 mesh particles for evaluation in the toluene conversion reactor described in Example 3 below. Following these steps should result in compositions having properties beneficial for use in the process of this invention.

EXAMPLE 3

A. Toluene Conversion Reactor

A stainless steel tube 20.32 centimeters (8 inches) in length and 0.95 centimeter (0.375 inch) in internal diameter having a usable capacity of 11 milliliters was employed as a reactor for the toluene conversion reaction. The reactor was arranged vertically and equipped at the upper end with reactant inlet means having calibrated flow controllers and vaporizers, and at the lower end with reaction effluent outlet means for collecting the reaction effluent or, alternatively, for direct introduction thereof via a gas sampling valve into a gas-liquid chromatograph for analysis. The outlet means was also equipped with means for introducting an inert gas diluent—nitrogen or helium, for example—into the reac-

TABLE 1

| SAMPLE NO. | $M_a^1M_b^2O_x$ | STARTING MATERIALS GRAMS (MOLES) $M^1$ | $M^2$ | ATOMIC RATIO $M^1/M^2$ | CALCINATION CONDITIONS TEMPERATURE, °C./TIME, HOURS INITIAL | FINAL |
|---|---|---|---|---|---|---|
| 1-A-1- | $Tl_aSb_bO_x$ | $Tl_2O_3$ | $Sb_2O_3$ | Tl/Sb | | |
| (a) | $TlSb_{0.33}O_x$ | 80.0 (0.18) | 17.0 (0.058) | 3 | 400/2 | 700/12 |
| (b) | $TlSb_{0.5}O_x$ | 70.0 (0.15) | 22.3 (0.077) | 2 | 400/2 | 700/12 |
| (c) | $TlSbO_x$ | 114.2 (0.25) | 72.9 (0.25) | 1 | 400/2 | 700/12 |
| (d) | $TlSb_2O_x$ | 50.0 (0.11) | 68.8 (0.22) | 0.5 | 400/2 | 700/12 |
| (e) | $TlSb_3O_x$ | 45.0 (0.099) | 86.8 (0.30) | 0.33 | 400/2 | 700/12 |
| 1-A-2- | $Tl_aTi_bO_x$ | $Tl_2O_3$ | $TiO_2$ | Tl/Ti | | |
| (a) | $TlTi_{0.2}O_x$ | 140.0 (0.31) | 10.0 (0.13) | 5 | 400/2 | 700/14 |
| (b) | $TlTi_{0.33}O_x$ | 130.0 (0.28) | 15.2 (0.19) | 3 | 400/2 | 700/12 |
| (c) | $TlTi_{0.5}O_x$ | 125.0 (0.27) | 22.0 (0.28) | 2 | 400/2 | 700/12 |
| (d) | $TlTiO_x$ | 110.0 (0.24) | 38.5 (0.48) | 0.5 | 400/2 | 700/12 |
| (e) | $TlTi_2O_x$ | 85.0 (0.19) | 60.0 (0.75) | 0.33 | 400/2 | 700/12 |
| (f) | $TlTi_3O_x$ | 70.0 (0.15) | 73.5 (0.92) | | | |
| 1-A-3- | $Tl_aTa_bO_x$ | $Tl_2O_3$ | $Ta_2O_5$ | Tl/Ta | | |
| (a) | $TlTaO_x$ | 11.4 (0.025) | 10.3 (0.23) | 1 | 400/2 | 700/12 |
| 1-A-4 | $Tl_aMn_bO_x$ | $Tl_2O_3$ | 50% $Mn(NO_3)_2$ | Tl/Mn | | |
| (a) | $TlMnO_x$ | 45.6 (0.10) | 70.6 (0.20) | 1 | 450/1 | 700/12 |
| 1-B-1- | $Tl_aLa_bO_x$ | $Tl_2O_3$ | $La_2O_3$ | Tl/La | | |
| (a) | $TlLaO_x$ | 45.6 (0.10) | 32.6 (0.10) | 1 | 400/2 | 700/12 |
| 1-B-2- | $Tl_aHo_bO_x$ | $Tl_2O_3$ | $Ho_2O_3$ | Tl/Ho | | |
| (a) | $TlHoO_x$ | 12.0 (0.026) | 10.0 (0.026) | 1 | 400/2 | 700/12 |
| 1-B-3- | $Tl_aU_bO_x$ | $Tl_2O_3$ | $U_3O_8$ | Tl/U | | |
| (a) | $TlU_{1.5}O_x$ | 26.5 (0.058) | 48.8 (0.058) | 1 | 400/1 | 700/12 | tion effluent for analysis purposes. A radiant furnace was used to maintain a constant temperature during the reaction period. The temperature was measured with a thermocouple in a temperature well located on the lower outside wall of the reactor.

B. Toluene Conversion

The reaction was conducted in the stoichiometric mode of operation unless otherwise noted. The reactor was charged with approximately 11 milliliters of the inorganic metal/oxygen composition prepared as described in Examples 1 and 2 above. Glass wool plugs were used as supports for the composition. The charged reactor was placed in a radiant furnace and heated to maintain a constant temperature throughout the reaction period. Steam and toluene in a 2:1 mole ratio were fed to the reactor at a pressure of $1.013 \times 10^5$ pascal (1 atmosphere) at a rate sufficient to provide a reactor resident (contact) time of 4 seconds (unless otherwise noted) for the toluene (assuming a 50% void space in the reactor). After the reaction had proceeded for 1 minute, the reaction effluent, diluted with helium, was analyzed by gas-liquid chromatography. The results are tabulated in Table 2.

TABLE 2

| SAMPLE NO. | TEMPERATURE, °C./ CONTACT TIME seconds[1] | CONVERSION % | SELECIVITY, % | | | |
|---|---|---|---|---|---|---|
| | | | STILBENE | BIBENZYL | BENZENE | STILBENE + BIBENZYL |
| 1-A-1-(a) | 630 | 92.0 | 24.5 | 2.7 | 21.8 | 27.2 |
| | 570 | 49.5 | 34.4 | 23.2 | 10.7 | 57.6 |
| | 450 | 13.2 | 14.1 | 26.6 | 3.4 | 40.7 |
| 1-A-1-(b) | 630 | 95.7 | 18.5 | 0.6 | 23.3 | 19.1 |
| | 570 | 80.3 | 55.5 | 3.7 | 9.8 | 59.2 |
| | 450 | 20.7 | 27.3 | 23.3 | 5.7 | 50.6 |
| 1-A-1-(c) | 630 | 50.0 | 18.1 | 13.7 | | |
| 1-A-2-(c) | | 31.8 | | | | |
| | 570 | 5.3 | 6.5 | 69.0 | 21.5 | 75.5 |
| | 480 | 0.6 | 0.0 | 26.7 | 61.8 | 26.7 |
| 1-A-1-(d) | 630 | 8.7 | 7.6 | 19.9 | 28.0 | 27.5 |
| | 570 | 10.1 | 7.7 | 17.5 | 41.5 | 25.2 |
| | 450 | 3.1 | 2.5 | 6.7 | 45.0 | 9.2 |
| 1-A-1-(e) | 630 | 23.8 | 6.1 | 16.1 | 37.1 | 22.2 |
| | 570 | 8.5 | 4.9 | 21.6 | 33.4 | 26.5 |
| | 450 | 7.8 | 1.0 | 11.0 | 9.4 | 12.0 |
| 1-A-2-(a) | 600 | 62.0 | 11.3 | 15.5 | 21.6 | 26.8 |
| | 480 | 13.4 | 21.9 | 48.4 | 4.4 | 70.3 |
| | 450 | 5.7 | 13.1 | 62.0 | 3.6 | 75.1 |
| 1-A-2-(b) | 600 | 65.9 | 26.9 | 14.0 | 15.6 | 40.9 |
| | 510 | 17.1 | 28.3 | 44.3 | 8.2 | 72.6 |
| | 450 | 5.5 | 15.4 | 61.3 | 9.4 | 76.7 |
| 1-A-2-c) | 600 | 95.8 | 30.7 | 0.1 | 26.0 | 30.8 |
| | 510 | 31.4 | 44.8 | 15.4 | 7.3 | 60.2 |
| | 450 | 6.7 | 15.7 | 36.0 | 8.6 | 51.7 |
| 1-A-2-(d) | 600 | 44.1 | 38.8 | 2.0 | 30.5 | 40.8 |
| | 510 | 27.5 | 72.2 | 4.7 | 11.6 | 76.9 |
| | 450 | 24.2 | 33.0 | 16.2 | 4.3 | 49.2 |
| 1-A-2-(e) | 600 | 7.2 | 21.4 | 2.7 | 38.4 | 24.1 |
| | 510 | 2.3 | 44.8 | 12.0 | 29.4 | 56.8 |
| | 450 | 3.3 | 27.0 | 15.2 | 50.3 | 42.2 |
| 1-A-2-(f) | 600 | 7.6 | 24.5 | 0.0 | 37.3 | 24.5 |
| | 510 | 2.3 | 44.4 | 3.3 | 37.5 | 47.7 |
| | 450 | 1.3 | | | | |
| 1-A-3-(a) | 630 | 83.2 | 47.2 | 2.0 | 34.0 | 49.2 |
| | 570 | 5.2 | 45.0 | 3.1 | 35.6 | 48.1 |
| | 450 | 17.1 | 0.8 | 0.5 | 45.9 | 1.3 |
| 1-A-4-(a) | 630 | 51.4 | 23.3 | 0.7 | 52.4 | 24.0 |
| | 570 | 29.0 | 46.1 | 0.2 | 39.4 | 46.3 |
| | 450 | 23.9 | 21.5 | 8.3 | 27.4 | 29.8 |
| 1-B-1-(a) | 630 | 61.1 | 26.2 | 0.7 | 69.2 | 26.9 |
| | 570 | 40.2 | 51.5 | 1.3 | 38.2 | 52.8 |
| | 450 | 53.7 | 9.0 | 0.9 | 83.7 | 9.9 |
| 1-B-2-(a) | 630 | 41.1 | 39.5 | 0.1 | 35.7 | 39.6 |
| | 570 | 28.2 | 41.8 | 1.9 | 28.8 | 43.7 |
| | 450 | 14.4 | 69.0 | 0.8 | 25.7 | 69.8 |
| 1-B-3-(a) | 630 | 43.1 | 4.6 | 0.3 | 91.3 | 4.9 |
| | 570 | 43.6 | 26.2 | 0.8 | 64.5 | 27.0 |
| | 450 | 10.0 | 48.9 | 3.2 | 40.5 | 52.1 |

[1] A contact time of 4 seconds was employed unless otherwise noted.

Thus, it is apparent that there has been provided, in accordance with the present invention, a process that fully satisfies the objects and advantages set forth hereinabove. While the invention has been described with respect to various specific examples and embodiments thereof, it is understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for dehydrocoupling toluene which comprises contacting the toluene in the vapor phase at a temperature between about 450° C. and about 650° C. with an inorganic metal/oxygen composition represented by the empirical formula:

$$M_a^1 M_b^2 O_x$$

where $M^1$ is thallium and $M^2$ is at least one element selected from arsenic, antimony, thorium, uranium, the lanthanides, Groups 3b, 4b, 5b, and 7b of the Periodic Table of the Elements, and mixtures thereof, and wherein a is 1, b is 0.01 to 10, and x is a number taken to satisfy the average valences of $M^1$ and $M^2$ in the oxidation states in which they exist in the composition to yield the dehydrocoupled toluene product.

2. The process of claim 1 wherein $M^2$ is selected from tantalum, antimony, and Group 4b of the Periodic Table of the Elements, and mixtures thereof.

3. The process of claim 2 wherein $M^2$ is titanium of Group 4b.

4. The process of claim 1 wherein steam is introduced with the toluene in an amount sufficient to provide a steam-to-toluene mole ratio between about 0.1 and about 10.

5. The process of claim 1 wherein b in the empirical formula representing the inorganic metal/oxygen composition in 0.5 to 5.

6. The process of claim 5 wherein the contacting between the toluene and the inorganic metal/oxygen composition is effected for a period between about 1 second and about 12 hours.

7. The process of claim 6 wherein the temperature is between about 500° C. and about 600° C.

8. The process of claim 1 wherein the dehydrocoupling reaction is conducted in a stoichiometric mode of operation in the absence of added free oxygen.

9. The process of claim 1 wherein a reactant selected from the group consisting of oxygen and an oxygen-containing gas is introduced with the toluene.

10. The process of claim 9 wherein the oxygen and oxygen-containing gas is introduced in an amount sufficient to conduct the dehydrocoupling reaction in a catalytic mode of operation.

11. The process of claim 10 wherein the oxygen and oxygen-containing gas is introduced in an amount sufficient to provide a toluene-to-oxygen mole ratio between about 1 and 8.

12. The process of claim 9 wherein the oxygen and oxygen-containing gas is introduced in an amount sufficient to conduct the dehydrocoupling reaction in a combined catalytic/stoichiometric mode of operation 13. The process of claim 1 wherein the inorganic metal/oxygen composition is admixed with a support material.

14. The process of claim 13 wherein the support material is a metal aluminate.

15. The process of claim 14 wherein the metal aluminate is calcium aluminate.

16. The process of claim 1 wherein the dehydrocoupling reaction is conducted at a toluene conversion level of about 20 to about 55 percent.

17. The process of claims 1, 2, 3, 4, 5, 6, 7, 8, 9, 10, 11, 12, 13, 14, 15, or 16 wherein the dehydrocoupled toluene product is stilbene.

* * * * *

UNITED STATES PATENT AND TRADEMARK OFFICE
CERTIFICATE OF CORRECTION

PATENT NO. : 4,243,825

DATED : January 6, 1981

INVENTOR(S) : Samuel J. Tremont, Alex N. Williamson

It is certified that error appears in the above-identified patent and that said Letters Patent are hereby corrected as shown below:

Column 1, line 17, delete "intermedidate" and substitute therefor -- intermediate --.

Column 2, line 21, delete "slectivities" and substitute therefor -- selectivities --.

Column 5, line 33, after "mode", delete "or" and add -- of operation or a combined catalytic/stoichiometric mode of --.

Column 10, Table 2, line 7 (in the tabulation portion) under the headings "BENZENE" and "STILBENE + BIBENZYL", respectively, add -- 35.8 -- and -- 31.8 --.

Column 10, Table 2, line 8 (in the tabulation portion) after "1-A-1-(c)", delete "1-A-2-(c)" and "31.8".

Column 11, line 29 (Claim 6), delete "hours" and substitute therefor -- seconds --.

Signed and Sealed this

Twelfth Day of May 1981

[SEAL]

Attest:

RENE D. TEGTMEYER

Attesting Officer

Acting Commissioner of Patents and Trademarks